US006921539B2

(12) United States Patent
Ninkov

(10) Patent No.: US 6,921,539 B2
(45) Date of Patent: Jul. 26, 2005

(54) ANTIMICROBIAL THERAPEUTIC COMPOSITIONS AND METHOD OF USE

(76) Inventor: Dusan Ninkov, 11839 Caminito Corriente, San Diego, CA (US) 92128

(*) Notice: Subject to any disclaimer, the term of this patent is extended or adjusted under 35 U.S.C. 154(b) by 0 days.

(21) Appl. No.: 10/370,411

(22) Filed: Feb. 18, 2003

(65) Prior Publication Data

US 2003/0176364 A1 Sep. 18, 2003

Related U.S. Application Data

(60) Provisional application No. 60/359,069, filed on Feb. 20, 2002.

(51) Int. Cl.[7] .................. A01N 25/32; A01N 25/02; A01N 25/10
(52) U.S. Cl. ............... 424/405; 424/406; 514/535; 514/536; 514/537; 514/642; 514/643
(58) Field of Search ................. 424/405, 406, 424/484–488; 514/817, 818, 729, 731, 535–537, 642, 643

(56) References Cited

U.S. PATENT DOCUMENTS 6,299,902 B1   10/2001  Jun et al.
6,509,492 B1 *  1/2003  Venkataraman .............. 560/68

* cited by examiner

Primary Examiner—Neil S. Levy
(74) Attorney, Agent, or Firm—O'Melveny & Meyers LLP

(57) ABSTRACT

The invention provides therapeutic antimicrobial compositions and methods for their use based on natural organic phenolic compounds combined with pharmacological agents. The antimicrobial activities of each carvacrol and thymol are believed to be enhanced, while the pharmacological properties of procaine and related compounds are added to provide their unique properties to facilitate usefulness and effectiveness in humans. The therapeutic compositions are active against bacterial, fungal, and protozoan infections. The forms of the invention are intended to treat various internal infections through parenteral, subcutaneous, intradermal, intravenous, and intramuscular injections. They are also intended as useful agents to treat microbial infections that have become resistant to conventional anitibiotics as well as secondary opportunistic infections.

8 Claims, 7 Drawing Sheets

US 6,921,539 B2

ANTIMICROBIAL THERAPEUTIC COMPOSITIONS AND METHOD OF USE

CROSS REFERENCE TO RELATED APPLICATIONS

This application claims priority to U.S. provisional application No. 60/359,069 filed on Feb. 20, 2002.

BACKGROUND OF THE INVENTION

1. Field of the Invention

The present invention relates to preparing therapeutics of an injectable solution containing carvacrol and thymol isolated from natural origins for intramuscular or intravenous application in the form of an organic complex compounded with pharmacological base agents for use in human and veterinary medicine.

2. Description of Related Art

Treatment of infectious diseases is primarily done with antibiotics, sulfonamides, steroid hormones, antifungal, and antiprotozoan compounds. Viral infections are more difficult to treat and limited drugs are available that treat them without significant side effects. In the case of bacterial and fungal disease, an increasing problem is the numbers of resistant and multi-drug resistant organisms. These necessitate the use of antimicrobial drugs that have more toxic side effects that can often lead to liver and kidney damage. Thus, the development of antimicrobial compounds from natural sources, such a medicinal herbs or plants, is an advantageous solution that addresses some of these concerns. The Lamiaceae and Labiatae families of plants are known to have useful medicinal properties. The related Verbenaceae family of plants also has similar medicinal characteristics.

The common name for members of the Labiatae, a large family of chiefly annual or perennial herbs, is the "mint family." The mint family is classified in the division Magnoliphyta, class Magnoliopsida, order Lamiales. The mint family includes about 200 genera, such as *Salvia* (sage), *Rosmarinus* (rosemary), *Mentha* (mint), *Ocimum* (basil), *Thymus* (thyme), *Marrubium* (hoarhound), *Monarda* (horse mint), *Trichostema* (bluecurls), *Teucrium, Hyptis, Physostegia, Lamium* (henbit), *Stachys, Scutellaria* (skullcap), *Nepeta* (catmint). Members of the Verbenaceae family include Lippia (Mexican Oregano) and *Lycopus*. The plants in the mint family are typically shrubby or climbing, although some exist as small trees. The plants are found throughout the world.

The mint family is well known for the aromatic volatile or essential oils in the foliage, which are used in perfumes, flavorings, and medicines. Among the more important essential oils are those derived from sage, lavender, rosemary, patchouli, and the true mints. Many of the commonly used herbs are from the mint family, e.g., basil, thyme, savory, marjoram, oregano, and the like.

Many of these plants such as catnip, pennyroyal, hyssop, self-heal, and the horehound of confectionery have a history of medicinal use in domestic remedies. Others are used as curative teas, for example, bee balm and yerba Buena.

The true mints belong to the genus *Mentha*. Catnip or catmint refers to a strong-scented perennial herb (*Nepeta cataria*) of the family Labiatae. Catnip is native to Europe and Asia and naturalized in the United States. Although best known for its stimulating effect on cats, tea of the leaves and tops of the catnip plant have long been used as a domestic remedy for various ailments. For example, dry leaves from *Nepeta cataria* have been used for the production of tea, to treat restlessness, nervousness, insanity, and as a tonic for colic and carminative.

Members of the Lamiaceae, Labiatae, and Verbenaceae families of plants contain two chemical compounds in their volatile oils that have antimicrobial activities, and are commonly referred to as carvacrol (5-isopropyl-2-methylphenol or isopropyl-o-cresol) and thymol (5-methyl-2[1-methylethyl]phenol or isopropyl-cresol). These both are monoturpene phenolic compounds and are potent antimicrobial agents. They are effective against bacteria, fungi, and protozoan pathogens. Furthermore, it is believed that they kill these organisms by disrupting their cellular membranes and do not select resistant members of these pathogens. They are also not toxic for animals, including humans, and have been used in natural herb form or in oil preparations from these plants for many centuries. The development of a broad spectrum antimicrobial compound is important given the increasing problems with antibiotic resistant organisms including bacteria, yeast, fungi, and protozoan species.

The antimicrobial activity of carvacrol and thymol containing compounds is recognized by people skilled in the art and been developed for use in birds and animals. For example, U.S. Pat. No. 5,990,178 discloses pharmaceutical compositions for treating a disease in poultry induced by hemoflagellates. The pharmaceutical compositions disclosed therein contain the monoturpene phenolic compounds carvacrol and thymol. Both of these compounds are can be synthetic or obtained from oil extract from plants such as *Origanum vulgaris, Thymus vulgaris, Mentha piperita, Thymus sepilum, Saturia hortensis, Saturea montana, Saturea subricata, Carum corticum, Thymus zugus, Ocimum gratisimum, Moranda pungata, Mosla jananoica*, and *Salva off cinalis*. The '718 patent shows that the carvacrol and thymol are effective in treating a histomoniasis protozoan infection in various birds. A problem exists in that such monoturpene phenolic compounds may cause irritation and pain and so are not well suited for use in humans.

Also, U.S. Pat. No. 6,322,825 discloses pharmaceutical compositions for treating gastrointestinal infections in animals. The pharmaceutical compositions disclosed therein contain carvacrol and/or thymol. Thymol and carvacrol which can be synthetic or obtained from plant oil extracts, such as *Origanum vulgaris, Thymus vulgaris, Mentha piperita, Thymus sepilum, Saturia hortensis, Saturea montana, Saturea subricata, Carum corticum, Thymus zugus, Ocimum gratisimum, Moranda pungata, Mosla jananoica*, and *Salva off cinalis*. In the '825 patent the use of the antimicrobial agents use is extended showing that the carvacrol and thymol containing compounds are effective against a large number of bacterial and fungal species. The application of such compounds is likely to result in significant gastrointestinal distress in humans precluding there use as therapeutic agents.

The U.S. Pat. No. 6,414,036 discloses compositions of carvacrol (isopropyl-o-cresol) and thymol (isopropyl-cresol) combined with Group I salts or organic acids that have antimicrobial activity. The compounds are effective against a broad number of bacterial, yeast, fungal, and protozoan species. Furthermore, the compounds are believed to have enhanced antimicrobial activity due to the reaction with Group I salts or organic acids. The compounds are proposed for use primarily in animal livestock, but also are proposed for use in humans. Despite the description of enhanced antimicrobial activity these compounds are still likely to cause irritation, pain, and distress when used in humans at therapeutic levels. The significant issue of pain and discomfort that are often associated with the use of monoturpene phenolic compounds based on carvacrol and thymol must be addressed to provide effective and useful human therapeutic compounds.

The application of such carvacrol and/or thymol compounds in therapies for human medicine must overcome certain problems that are less important in veterinary uses. One major concern is the irritation, discomfort, and pain that can result from the injection of monoturpene phenolic compounds, such as carvacrol and thymol. It is desirable to have an injectable formulation of carvacrol and thymol for treatment of internal human infections that is effective and does not cause pain or discomfort. Such a drug is also useful for veterinary medicine. An injectable agent allows treatment of internal infections in a quick timely manner that increases the chances of recovery. The dose of antimicrobial compound is also more constant and can be maintained better at therapeutic levels easier in an injectable form. If left unchecked or if treatment is slow, microbial infections can result in death even when effective conventional therapies are employed. Therefore, it would be desirable to provide an injectable form of carvacrol and thymol to achieve a more effective, pleasing, and reliable way to deliver the antimicrobial agents in doses that can be sustained over the time required to treat infectious diseases.

SUMMARY

This disclosure provides antimicrobial therapeutic compositions that are believed to have enhanced broad based antimicrobial activity and to be effective and useful for treating infections, especially in humans, though the compositions are also thought to be effective for use in other animals. The combination of an organic phenolic compound with either a local anesthetic, sympathomimetic, or an analgesic compound provides novel compositions that have strong antimicrobial activity and that also reduce pain and/or irritation associated with the administration of organic phenolic compounds. The organic phenolic components are typically the natural agents carvacrol and thymol, that can be isolated from the volatile essential oils of plant species that are members of the Lamiaceae, Labiatae, and Verbenaceae families. The organic phenolic compound and pharmacological base agent are combined either in a chemical reaction, or in mixtures.

The volatile essential oils of some plants also contain natural tannins, natural polyphenolic molecules, and/or hypericine, all of which posses antimicrobial activities and that are also capable of being components of antimicrobial compositions, similarly to carvacrol and thymol. In addition, the antimicrobial compositions of the present invention may be supplemented with various vitamins, minerals, amino acids, fats, and oils to aid in health and homeostasis. The local anesthetics procaine and lidocaine are well suited to provide their pharmacological anesthetic activity to reduce pain and/or irritation associated with the organic phenolic component. Other pharmacological compounds that are contemplated and may be combined with the antimicrobial organic phenolic compounds are ephedrine, hexylcain, propipocain, hydroxyamphetamine, valamine, gastrotest, and analexin, among others. The antimicrobial component of the overall therapeutic compositions are usually up to about ten percent of the total with the remainder being made up of a pharmaceutically acceptable carrier.

The antimicrobial compositions of the present invention are useful for treating numerous bacterial, yeast, fungal, protozoan, and parasitic infections in humans and other animals. They are also useful in treating opportunistic or secondary infections that result from primary viral infections, age, general poor health, and from a compromised immune system. They are also believed to be useful against microbes that have developed resistance to conventional antibiotics. The antimicrobial therapeutics are intended to be administered as sterile parenteral solutions via injection. They are intended to be used primarily as human antimicrobial therapeutics. A number of different formulations can be manufactured depending on the type and location of the infection to be treated.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE PREFERRED EMBODIMENT

Figure 1A:
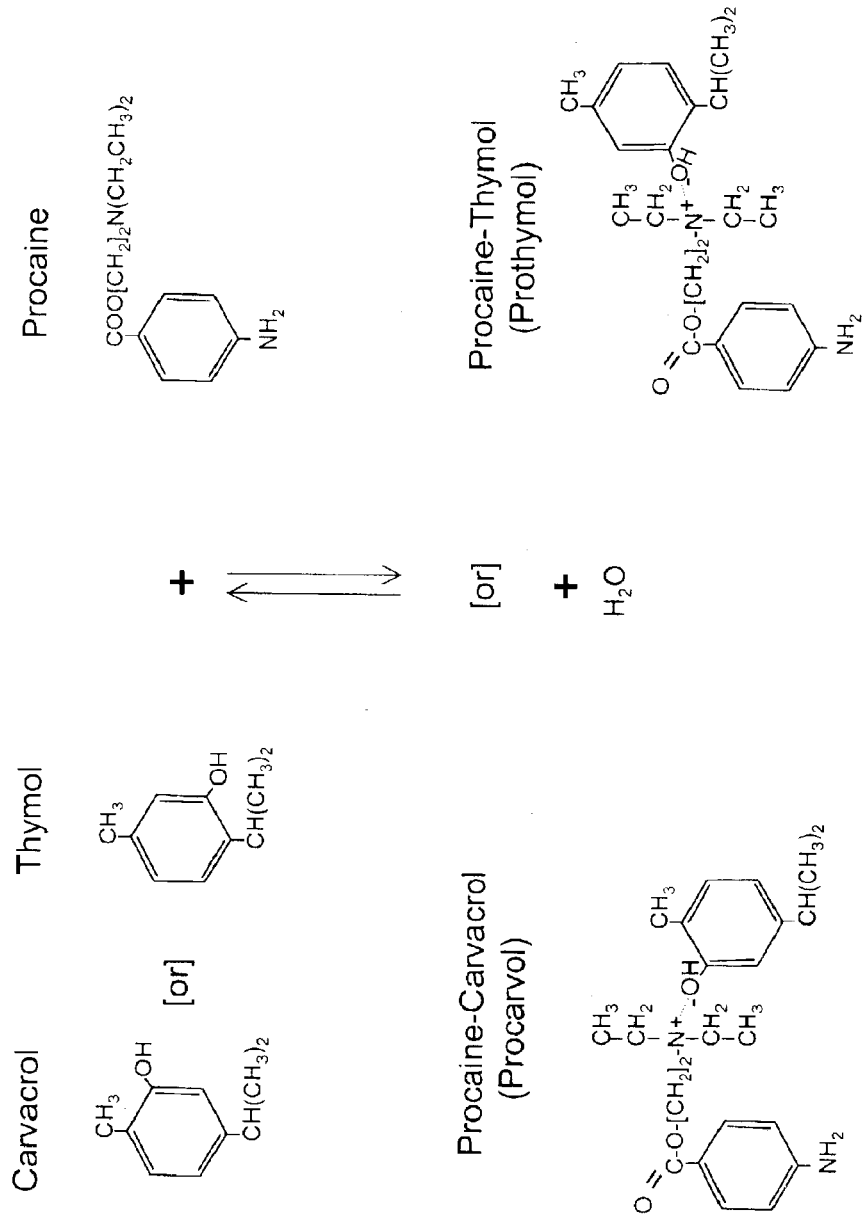
FIGS. 1A and 1B illustrate a schematic reaction of carvacrol (isopropyl-o-cresol) and thymol (isopropyl-cresol) with procaine and lidocaine.
Figure 1B:
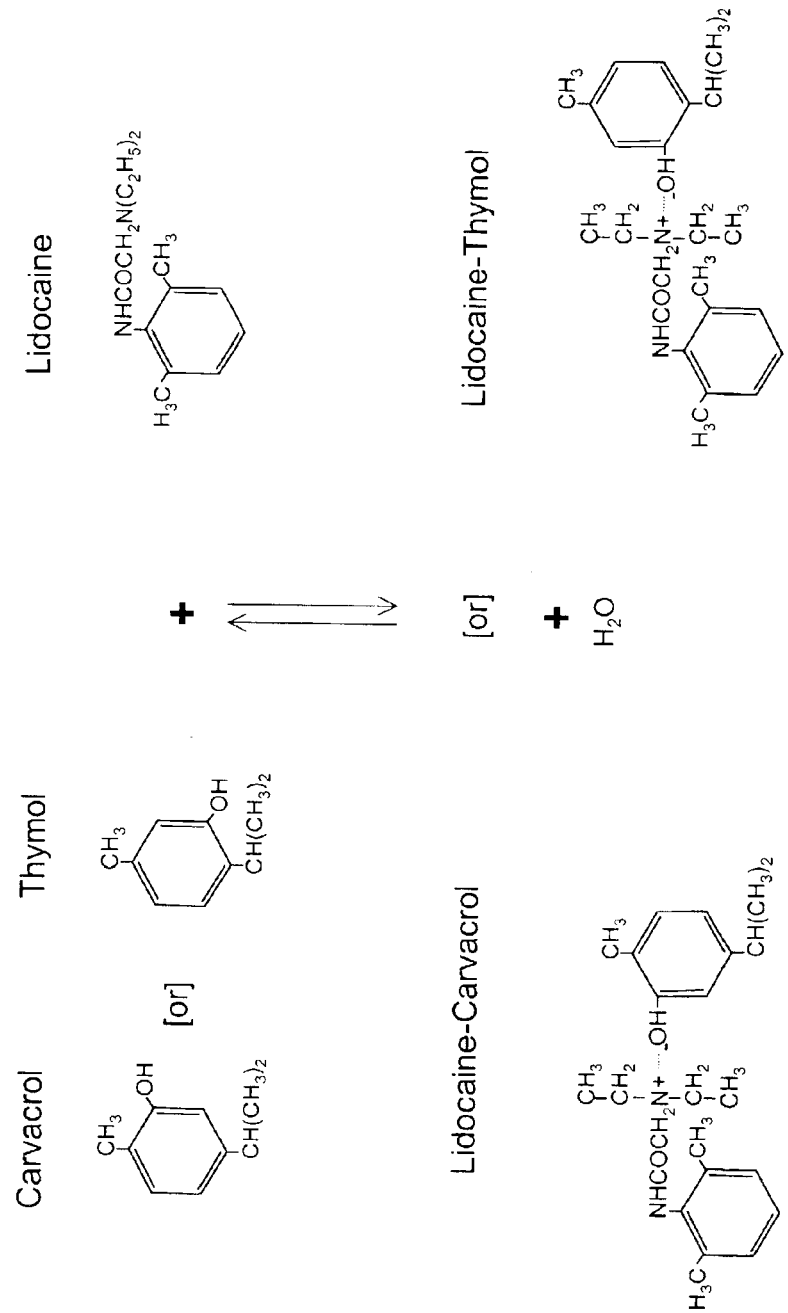

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

The invention provides pharmaceutical therapeutic compositions that include an oil extract from plants from the Lamiaceae, Labiatae, and Verbenaceae families. In particular, the antimicrobial pharmaceutical compositions include an organic phenolic compound, such as carvacrol (isopropyl-o-cresol or 5-isopropyl-2-methylphenol) and/or thymol (isopropyl-cresol or (5methyl-2[1-methylethyl] phenol). The organic phenolic compounds are ideally obtained from plant oil extracts, but can also be synthesized by known methods. In one embodiment, the organic phenolic compound is combined with an anesthetic, such as procaine and/or related derivatives to form an antimicribial compound. In another preferred embodiment, the organic phenolic compound is compounded with either lidocaine or ephedrine. In other embodiments, similar local anesthetics, simpathomimetic compounds, analgesics, or the like compounds, may be combined with either carvacrol or thymol to form antimicrobial compounds. Both the unreacted organic phenolic compound and the anesthetic procaine reacted organic phenolic compounds, lidocaine reacted organic compounds, and ephedrine reacted compounds, are referred to herein as "antimicrobial compounds". The association of pharmacological agents both balances the acidic character of the carvacrol or thymol and results in an improved tolerance by minimizing irritation, discomfort, and pain. They also provide anesthetic, analegesic, sympathomimetic, or stimulant activities that contribute to overall homeostasis. These pharmacological base compounds improve the effectiveness of the antimicrobial compounds and provide relief from unpleasant effects of the organic phenolic carvacrol or thymol molecules.

The therapeutic pharmaceutical compositions represented by the embodiments are suitable for treating internal microbial infections and internal inflammation processes by administering them to animal primates such as, for example humans, apes, and monkeys; and other animals such as, for example, livestock, horses, cows, pigs, sheep, goats, rabbits; rodents; pets such as, for example, dogs, cats, and birds; and poultry such as, for example, chickens, turkeys, and ducks.

Because the antimicrobial compounds are degraded by enzymes, the pharmaceutical compositions are particularly well suited for treating microbial infections in humans as well as other animals. Organic phenolic compounds such as carvacrol (isopropyl-o-cresol) and thymol (isopropyl-cresol) are degraded by enzymes into inactive metabolites. The metabolites can be excreted in the urine (approx. 90%) or expired from the lungs (10%) in the form of carbon dioxide ($CO_2$). Mechanisms of degradation of isopropyl-o-cresol and isopropyl-cresol are well known in the art.

The metabolic fate of local anesthetics are important since their toxicity depends on their rate of absorption and destruction. The ester-type anesthetics, such as procaine are hydrolyzed by both plasma and hepatic (liver) esterases. The plasma esterase activity is high in humans and accounts for a majority of degradation of the ester-type anesthetics. The amide-type anesthetics such as lidocaine are primarily degraded by hepatic microsomes via N-dealkylation and hydrolysis (Remington $20^{th}$ Edition. H. Steve White, Ph.D. Local Anesthetics p1400–1406).

The antimicrobial compounds of the present formulations do not appear to be mutagenic or carcinogenic. Furthermore, it is believed that the efficacy of the antimicrobial compounds will not be compromised because of pathogen resistance. It is believed that the activity of the antimicrobial compounds are similar to the activity of benzyl alcohol, phenol, and polyphenols in that the antimicrobial compounds destroy the cell membranes of the microorganism to cause cell death. Since it is believed that the antimicrobial agents of the present embodiments share this mechanism of cellular destruction, they will not result in the development of resistant microorganisms. As used herein, the term "antimicrobial activity" includes bactericidal, fungicidal, protozoanicidal, antiparasitic and other disinfective activity.

I. Antimicrobial Organic Phenolic Compounds

The antimicrobial compounds of the invention include an organic phenolic compound, such as carvacrol (isopropyl-o-cresol; or 5-isopropyl-2-methylphenol) or thymol (isopropyl-cresol, or 5-methyl-2[1-methylethyl]phenol). In one embodiment, the antimicrobial compound is an organic phenolic compound combined with an organic analgesic base, such as procaine. In another preferred embodiment, the organic phenolic compound is compounded with either lidocaine or ephedrine. In other embodiments, local anesthetics, simpathomimetic compounds, analgesics, or like related agents may be combined with either carvacrol or thymol to form antimicrobial compounds.

Organic phenolic compounds can ideally be isolated and purified from plant oil extracts, or also made synthetically by known methods. Carvacrol (isopropyl-o-cresol) is a crystal with a boiling point of about 233° C. at atmospheric pressure. Thymol (isopropyl-cresol) is a liquid that has a boiling point at atmospheric pressure of 237–238° C. Both compounds volatilize in water vapor. Preferably, the oil is extracted from a member of the Lamiaceae, Labiatae or Verbenaceae family. The Labiatae family includes about 200 genera, such as *Salvia, Rosmarinus, Mentha, Ocimum, Thymus, Marrubium, Monarda, Trichosterna, Teucrium, Hyptis, Physostegia, Lamium, Stachys, Scutellaria* and *Lycopus*. Suitable plants include, but are not limited to, *Ocimum* spp., *Saturea* spp., *Monarda* spp., *Origanum* spp., *Thymus* spp., *Mentha* spp., *Nepeta* spp., *Teucrium gnaphalodes, Teucrium polium, Teucrim divaricatum, Teucrim kotschyanum, Micromeria myrifolia, Calamintha nepeta, Rosmarinus officinalis, Myrtus communis, Acinos suaveolens, Dictamnus albus, Micromeria fruticosa, Cunila origanoides, Mosla japonoica, Maxymowitz, Pycnanthemum nudum, Micromeria juliana, Piper betel, Trachyspermum antmi, Lippia graveolens,* as well as others. In one preferred embodiment the carvacrol and thymol containing oils are purified from the species *Origanum vulgare* of a hirtum variety. Ideally this is a hybrid strain that produces high quality oils, but is not limited to this species and strain. In another preferred composition, the oil extract is from plant of the species *Nepeta* including, but not limited to *Nepeta racemosa* (catmint), *Nepeta citriodora, Nepeta elliptica, Nepeta hindostoma, Nepeta lanceolata, Nepeta leucophylla, Nepeta longiobracteata, Nepeta mussinii, Nepeta nepetella, Nepeta sibthorpii, Nepeta subsessilis* and *Nepeta tuberosa.*

Organic phenolic compounds, such as carvacrol (isopropyl-o-cresol) and thymol (isopropyl-cresol) are soluble in lipids. It is believed that the antimicrobial activity of the organic phenolic compounds is due to the destruction of lipids in the microorganism's cell membrane.

II. Extraction of Carvacrol and Thymol from Plants

A. Cultivating the Plant

Plants of the Lamiaceae, Labiatae and Verbenacea families are found throughout the world and are relatively easy to cultivate. To cultivate the plants, seeds, preferably those with a high percentage of phenolic compounds are planted in fine loose soil, preferably in a sub-tropical climate (containing about 70 wt % to about 80 wt %, of organic phenolic compound). Hybrid seeds having a high percentage of organic phenolic compounds can be produced by known techniques. The seeds are then cultivated using known agricultural techniques, such as watering and artificial fertilizing.

Because the leaves contain a high amount of oil upon blossoming, it is preferred that the plants be harvested soon after the plants begin to blossom. Preferably, the plants are harvested within 24 hours after blossoming, more preferably within 12 hours after blossoming. Most preferably, harvesting is undertaken early in the morning or late in the evening hours when the leaves are not exposed to the sun.

Because the majority of the oil is found in the leaves and blossoms of the plant, it is preferred that the leaves and blossoms be utilized in the extraction process. Use of other parts of the plant may increase impurities and decrease yield.

B. Extracting Oil from the Plant

Oil containing organic phenolic compounds can be extracted from either dried or fresh plants, or both. If the plant is dried, the drying process is preferably undertaken in drying houses that are constructed to allow constant, free circulation of air. Preferably, the harvested leaves and blossoms should not be exposed to direct sunlight, as exposure to sunlight may reduce the amount of active material present in the leaves.

To dry the product, the leaves and blossoms are arranged in layers of 20–25 cm thick. To promote uniform drying, the layers should be turned up-side-down either manually or mechanically daily, preferably more than once a day, more preferably multiple times a day, such as four times a day, preferably during the first few days of drying, typically within the first three days. Generally, the leaves are dried for about 7 to 8 days.

After the leaves and blossoms are dried, the oil can be extracted by known methods, including distillation, for example, steam distillation. Preferably, the oil is extracted in a two stage distillation process (double distillation). The oil is first extracted by steam distillation (at a temperature of about 100° C.) to remove most impurities. Typically, after the first steam distillation, the extracted oil contains about 3% to about 4% by weight thymol (isopropyl-cresol); about 60% to about 70% carvacrol (isopropyl-o-cresol). If desired, the solid base-reacted antimicrobial compound can be purified, for example, by recrystallization.

The development of new improved purification methods allows isolation of carvacrol (isopropyl-o-cresol) and thymol (isopropyl-cresol) at purity levels in excess of 98–99%. The quantitative content of carvacrol (isopropyl-o-cresol) and thymol (isopropyl-cresol) can then be determined using, but not limited to, gas chromatographic methods. The new method of purification is believed to enhance the antimicrobial properties of the carvacrol (isopropyl-o-cresol) and thymol (isopropyl-cresol).

C. Purification Facility: Coupled Vacuum Distillation and Fractionation

Figures 1, 2:
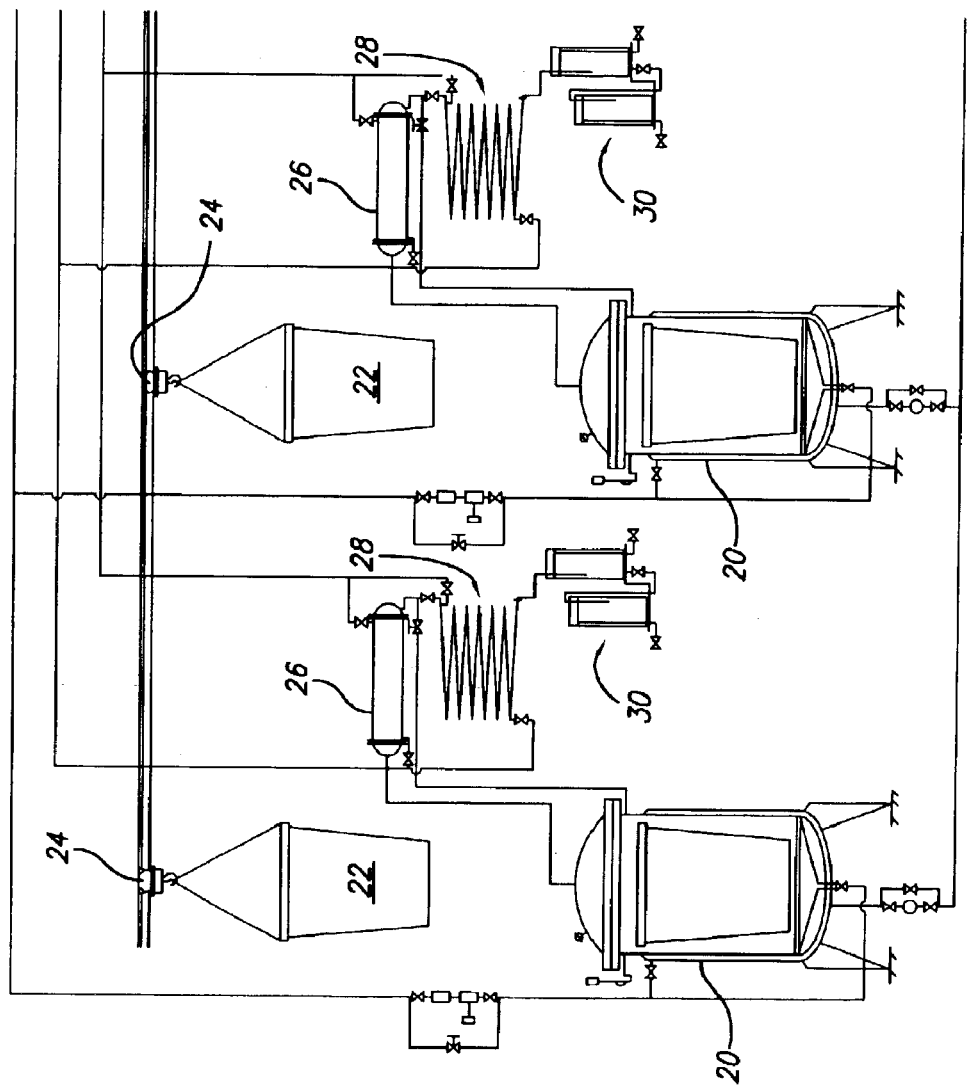
FIG. 2 is a diagram that illustrates the improved purification facility and method for isolating carvacrol and thymol in highly purified forms for use in formulations of the present invention.
Figure 2:
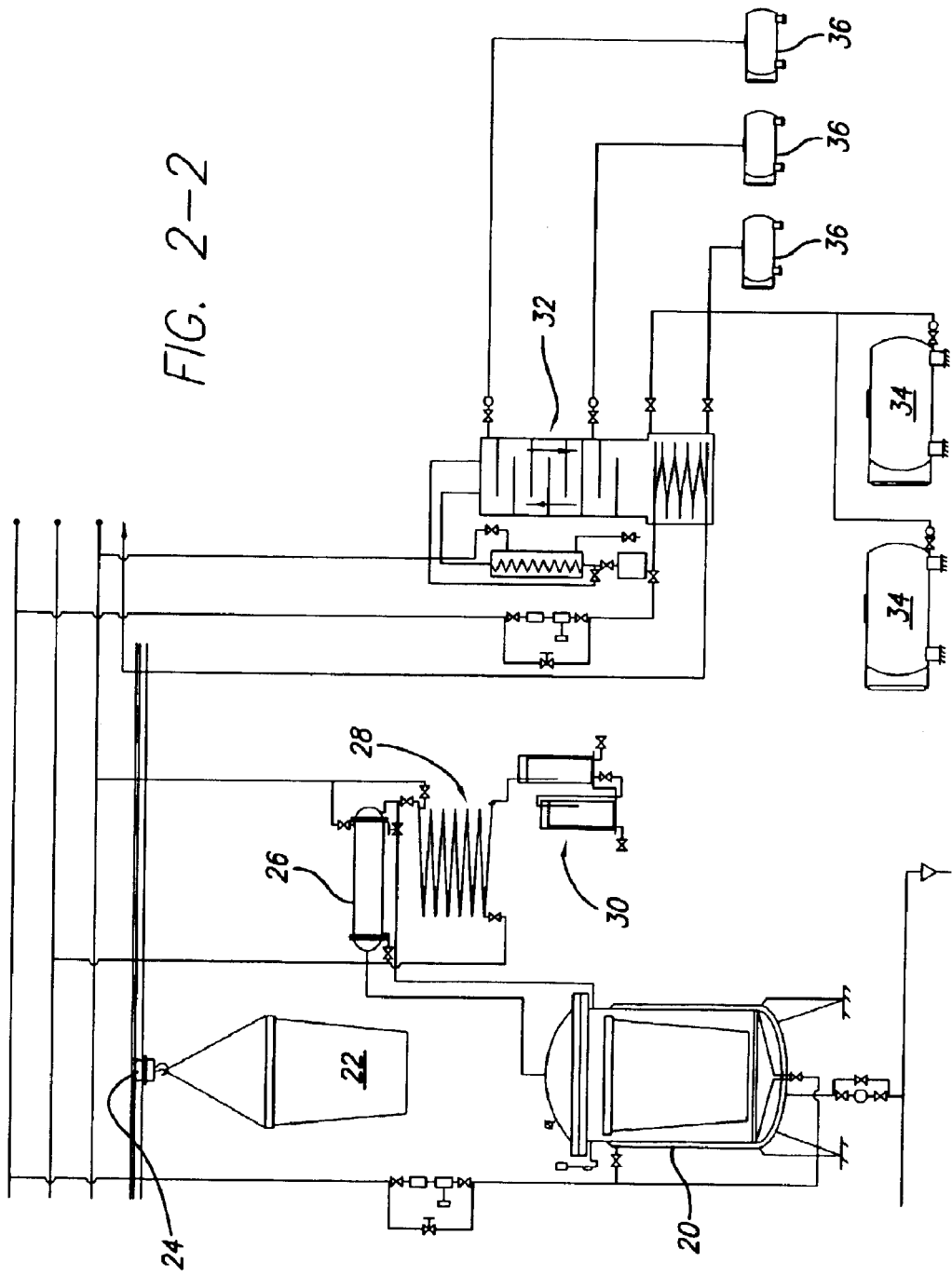

The purification facility is illustrated in FIG. 2. It is unique in the vacuum distillation and fractionation processes are coupled ensuring the oils are of the highest quality with increased purity and yield of the final products (FIG. 2). The improvements also result in increased efficiency and cost savings.

In order to hasten the distillation process the herb/plant material will be fragmented in stainless steel units (not depicted) fitted with blades of the same material. The herb/plant components are ideally fragmented about 15–20 minutes prior to the start of distillation. This augments the preservation of the highly volatile oils. The following medicinal herb/plant material can be distilled in the production facility: leafs, stems, flowers, roots, and the fruit from fresh or dried plants.

Subsequently, the herb/plant material is processed to purify the volatile ether oils by the facility depicted in FIG. 2. The herb/plant material is placed into stainless steel buckets/cradles with perforated bottoms 22. The central part of the bucket/cradle is approximately 0.2 m in diameter and approximately 1 m long. This allows for easier passage of water vapor and connection to the column in the distillation unit 20. A self propelled overhead crane 24 is mounted above a bank of three distillation units 20 for the transportation of the fragmented herb/plant material in the buckets/cradles 22 to the individual distillation units 20. Each distillation unit 20 has the capacity to handle approximately 400 to 900 kilograms (kg) of material and can withstand a vacuum rating of about 0.9 bar or absolute pressure rating of about 0.1 bar. The distillation units 20 are fitted with hydraulic lids and easy opening fly bolts for ease of use. The pipe connection to the distiller from the top includes a joint and/or elbow to allow for movement as the pipe is released from its lid/cover. This is a fast detachable connection. Undoing the fly nuts allows removal of the pipe connection and activation of the hydraulic (opening or closing) of the lid. There are two buckets/cradles 22 for each distillation unit 20 to increase the efficiency of the process.

A steam generator (not depicted) ideally provides at least 1000 kg per hour (h) of steam suitable for purification of carvacrol (isopropyl-o-cresol), thymol (isopropyl-cresol) and menthol (hexahydrothymol) products. The steam will be transported through receiving groups to the distilling units 20 at controlled temperature and pressure. It is important to maintain temperature regulation as the essential oils to be isolated are not stable at high temperatures. Oxidation may take place when temperatures are greater than 50° C. The vacuum distillation method employed avoids maceration of the oils at high temperatures. One unique feature of the facility is the way in which vacuum is provided in the distillation process. A compressor (not depicted) is used to provide the require vacuum. The compressor is simply fitted to the part of the piping connecting the distillation unit 20. In prior art facilities the vacuum is provided by vacuum pumps that result in large losses of the precious oil products. This does not occur with the compressor. The present method of creating vacuum results in recovery of up to 40% more oil compared to facilities using vacuum pumps. The compressor features may be as follows: Inlet about 0.1 bar (vacuum about 0.9 bar); Outlet about 1.1 bar; Capacity about 4 $m^3$. The compressor is a screw-type that does not use oil as a lubricant.

The volatile ether oil is extracted in the steam passing through a column in a distillation unit 20, i.e., through the fragmented herb/plant material in the buckets/cradles 22, and will be carried to a drum shaped condenser 26 for condensation, which takes place in two stages. In the first stage, on leaving the distillation unit 20, the vapor enters the drum shaped condenser 26 in which a major amount of the oil is condensed. The condenser 26 is of a unique design. The condenser 26 contains a receiver area, that the vapor from the distillation unit first enters, and which ensures that the vapor is evenly distributed in all pipes. It should be noted that the condenser 26 is designed such that there are no sudden cross sections, large curves, or pockets where oil would be retained. This is a major defect and problem in existing distillation facility condensers, where up to 15% of oil retained in the condensers is recovered by cleaning and pressurized blowing. This has a significant deleterious affect on the quality of the oil produced. Also the condenser 26 has incorporated additional outlets or drains within the receiver to increase oil recovery. These are arranged so that oil leaving the receiver contains a low water percentage, utilizing the differences in density between oil and water. Thus, the percentage of oil that is lost or retained in the receiver and condenser body is less than 0.1% of the total oil recovered from a single cycle of operation.

In the second stage of condensation, the remaining part of uncondensed water vapor and essential oil vapor, together with essential oil and water, enters a "tube to tube" second condenser/cooler 28 in which the condensation is completed. It then passes into glass decanters 30 (vessels for the separation of liquid). The decanters 30 are made of glass to allow the quantity of the ether oil to be measured. The advantage in having the tandem condensers 26 and 28 is their construction and proximity to each other that provides efficient transport of higher quality and increased amounts of the oil to the decanters. The oil will be transported from the decanters into stainless steel tanks 34 for immediate fractionation. The oil in the tanks 34 is moved into the fractionation column by forklifts.

The volatile ether oils is fractionated on uniquely large columns 32. Each column 32 is larger than previous columns and has bell like bottoms on which the ether oil fraction will be separated. The increase in column size increases the quality and purity of the oil produced. The column 32 floors are oversized to decelerate the fractionation process and provide as great an exchange volume as possible between the liquid and gaseous phases/stages. An advantage of the present columns 32 is that the floors can be removed from the column itself to allow different oils, such as carvacrol (isopropyl-o-cresol) and thymol (isopropyl-cresol), or other oils, to be purified. Each column 32 has outlets through which fractions will be transported to stainless steel tanks 34. The oil is transported into the large 34 tanks by pumps. These large tanks 34 are used for oil storage and transport within short time periods. The small tanks 36 are used exclusively for storage and include thermometers and are lined with insulation. They also have an extra opening in addition to the main one to allow samples to be taken for chemical analysis.

The quantitative content of carvacrol (isopropyl-o-cresol) and thymol (isopropyl-cresol) can then be determined using, but not limited to, chromatographic methods. These can include certain chromatographic methods, including but not limited to solid-liquid, liquid-liquid, and gas-liquid type chromatography. Examples of solid-liquid type chromatographic methods that could be utilized include column chromatography, gel chromatography, dry-column chromatography, or high performance liquid chromatography (HPLC).

The present method of purification is believed to enhance the antimicrobial properties of the carvacrol (isopropyl-o-cresol), thymol (isopropyl-cresol) due to increased purity and quality. The unique coupled distillation and fractionation process increases the speed and ensures the purity and quality of the final products. The cost of production is also reduced.

III. Synthetic Production of Organic Phenolic Compounds

Methods for synthetically producing organic phenolic compounds such as carvacrol (isopropyl-o-cresol) and thymol (isopropyl-cresol) are known in the art. Also, many of these compounds are available from chemical manufacturers and are listed in the Merck Index. Both synthetic carvcrol and synthetic thymol, as well as other synthetic organic phenolic compounds, are suitable for combining with procaine, and the other compounds listed in Table 1, to form antimicrobial compounds of the present invention. Additionally, synthetic organic compounds, such as synthetic carvacrol and synthetic thymol, may be combined with a variety of similar local anesthetics, simpathomimetics, and analgesic compounds, many of which are known in the art. However, it is generally preferred that the organic phenolic compound be extracted from plants instead of being chemically synthesized. Because phenol is often used to synthesize carvacrol (isopropyl-o-cresol) and thymol (isopropyl-cresol), the resulting synthetic product tends to contain residual phenol (lss than 1%). It may be undesirable to administer a composition containing phenol to an animal including humans because phenol can be mutagenic and carcinogenic. In addition the phenol may cause irritation, pain, discomfort, and damage in animals or humans.

IV. Organic Pharmacological Agents

Carvacrol (isopropyl-o-cresol) and thymol (isopropyl-cresol), belong to a group of monoturpene phenolic compounds. It is well known that phenol, as well as alcohols, contain an OH group. In the case of alcohols, the OH group is most often bound to an alkali group while with phenol the OH group is directly bound to the aromatic core. This is the case with carvacrol and thymol, which each have a benzene core that is similar in chemical properties to phenol. Due to the possibility of stabilizing the phenol union, the OH group is easily ionized, i.e., it easily releases the $H^+$ (proton), which makes phenol group containing molecules weak acids. This acid feature of the phenol moiety may be balanced by adding an organic base, or related compound.

In Table 1, representative pharmacological organic bases that may be combined with the antimicrobial phenolic acids carvacrol and thymol, are listed. One of ordinary skill in the art will appreciate that this list is not exhaustive but merely representative of the myriad of organic bases that may be used to practice embodiments of the present invention. In a preferred embodiment, the organic base is the local anesthetic procaine. In other preferred embodiments, the organic base pharmacological agent is lidocaine or ephedrine. In other embodiments similar local anesthetics, sympathomimetic compounds, analgesics, or like related agents may be combined with either carvacrol or thymol to form antimicrobial compounds. In further embodiments, the base can be from, but not limited to, the compounds listed in Table 1.

TABLE 1

| TRIVIAL NAME | CHEMICAL NAME | MOLAR MASS | PHARMACOLOGICAL EFFECT |
|---|---|---|---|
| Procaine | 2-(diethylamino)ethyl ester | 236.30 | Local anesthetic |
| Lidocaine | 2-(Diethylamino)-N-(2,6-dimethyl-phenyl)acetamide | 234.33 | Local anesthetic |
| Ephedrine | 2-methylamino-1-phenylpropan-1-ol | 165.23 | Sympathomimetic |
| Hexylcaine | 1-(cyclohexylamino)-2-propanol benzoate | 261.40 | Local anesthetic |
| Propipocaine | 3-(1-Piperidinyl)-1-(4-propoxyphenol)-1-propanone | 275.38 | Local anesthetic |
| Hydroxy-amphetamine | 4-(2-aminopropyl)-phenol | 151.21 | Sympathomimetic |
| Valamine | 1-Ethyleiklohexyl carbonate | 167.20 | Hypnotic |
| Gastrotest | 2,6 diamino-3-phenylazopiridin | 213.20 | Urogenital analgesic |
| Analexin | 1-phenyl-2(pirid-1-ilamino)ethanol | 214.30 | Analgesic |

Combining carvacrol (isopropyl-o-cresol) and thymol (isopropyl-cresol) with the organic pharmacological agents increases their ability to dissolve in water. This process is aided by binding the two molecules in a complex of an acid base type, while at the same time the antimicrobial effect of the compound is increased due to the pharmacological activity of the base agent. Also any irritation, discomfort, or pain from having formulations of the phenolic compounds of the preferred embodiment or other embodiments injected is reduced or eliminated by the pharmacological activity of the base agent. The resulting antimicrobial compounds are thus more effective for use in treating infections in humans.

V. Reaction to Form Antimicrobial Compound

As used herein, the term "antimicrobial compound" refers to both unreacted organic phenolic compounds and compounds formed by reacting an organic phenolic compound extracted from a plant of the Lamiaceae, Labiatae and/or Verbenacae family with an organic base that contains pharmacological activities. In some instances, the antimicrobial compound formed by reacting an organic phenolic compound with a base may be referred to as a "base reacted" compound. The antimicrobial compound may also be referred to as the "active ingredient or agent." An "antimicrobial compound" may refer to a compound formed by chemically reacting carvacrol (isopropyl-o-cresol) or thymol (isopropyl-cresol) with procaine, lidocaine, ephedrine, or other chemicals listed in Table 1, but is not limited to these agents.

As used herein, the term "reacting" refers to a process in which the organic phenolic compound is chemically modified (as compared to the formation of a solution). In the formation of the new antimicrobial compound by reaction with a pharmacological base a new chemical compound is made that is distinct and has increased antimicrobial activity and effectiveness (see Table 1, FIG. 1).

A. Antimicrobial Formulations

Bearing in mind the molecular weight of the pharmacological agents described in Table 1 a preferred formulation reaction of carvacrol (isopropyl-o-cresol) or thymol (isopropyl-cresol) with the Table 1 agents is shown in Table 2.

TABLE 2

|  | Amount (g) |
|---|---|
| Carvacrol (C)/ Thymol (T) | |
| C/T | 150.21 |
| C/T | 150.21 |
| C/T | 150.21 |
| C/T | 150.21 |
| C/T | 150.21 |
| C/T | 150.21 |
| C/T | 150.21 |
| C/T | 150.21 |
| C/T | 150.21 |
| Pharmacological Base Agent | |
| Procaine | 236.31 |
| Lidocaine | 234.34 |
| Ephedrine | 165.23 |
| Hexylcaine | 261.40 |
| Propipocaine | 275.38 |
| Hydroxyamphetamine | 151.21 |
| Valamine | 167.20 |
| Gastrotest | 213.20 |
| Analexin | 214.30 |

The exact optimal ratio of components is believed to be equimolar, though other ratios will be tested empirically to find the most effective antimicrobial activity while reducing any potential side effects such as, irritation, discomfort, or pain. It is not believed that these antimicrobial compounds will have any significant toxicity. In one embodiment, the antimicrobial compound generated by the reaction of the pharmacological agent from Table 1 with carvacrol (isopropyl-o-cresol) is combined with an antimicrobial compound formed by reacting the same agent with thymol (isopropyl-cresol). This is done by thoroughly mixing the two for 10 minutes by stirring. In a preferred formulation, the carvacrol (isopropyl-o-cresol) reacted base compound is combined with the thymol (isopropyl-cresol) reacted base in a ratio of 90:10. In other embodiments, the procarvol reacted compound is combined with the second thymol reacted compound in other ratios of: 95:5, 85:15, 80:20, 75:25, 70:30, 65:35, 60:40, 55:45, and 50:50 in the mixture. In other embodiments, the carvacrol reacted base compound is combined with the thymol reacted base compound still in other ratios. Still other embodiments can contain only carvacrol (isopropyl-o-cresol) reacted base compound or thymol (isopropyl-cresol) reacted base compound. Other contemplated antimicrobial compounds that can be reacted with pharmacological base compounds to form therapeutics in separate embodiments include hypericine and natural tannins or natural polyphenols. Hypericine is the active antimicrobial compound found in extracts from the plant *Hypericum perforatum*, commonly known as Saint John's wort, while a mixture of tannins is the antimicrobial compound found in the plant *Salvia Officinalis*, commonly known as English Sage. Natural tannins are also found in a wide variety of related plant species. Hypericine and natural tannin polyphenols can also be reacted with procaine, lidocaine, ephedrine, and like compounds to make unique antimicrobial therapeutics and are considered alternative embodiments. The reaction with the pharmacological compounds and like compounds would be by similar chemical reaction mechanisms.

In addition the organic phenolic compounds carvacrol and thymol may be combined in mixtures with the pharmacological base agents in Table 1 to form antimicrobial therapeutics. In these embodiments the individual compounds would be distinct entities, but would function together to provide antimicrobial as well as the specific activities of the pharmacological agents. The ideal ratios could be determined by experimentation and may vary with different infections or the location of the infection.

The essential oils of numerous plant species of the Lamiaceae, Labiatae and/or Verbenacae families also contain organic acids, alcohols, aldehydes, ketones, esters, other phenols, phenol esters, and many more complex organic compounds, many of which possess antimicrobial or other pharmacological activities. These include but are not limited to the organic acids acetic benzoate, cinnamic, and phenylacetic. They include, but are not limited to the alcohols benzyl alcohol, borneol, cinnamyl alcohol, citronellol, geraniol, linalool, menthol, phenylethyl alcohol, terpineol. They include, but are not limited to the aldehydes anisaldehyde, cinnamaldehyde, benzaldehyde, citral, piperonal, heliotropin, salicylaldehyde, and vanillin. They include, but are not limited to the ketones carvone, camphor, menthone, thujone, and pulejone. These include, but are not limited to the esters bornyl acetate, methyl salicylate, benzyl benzoate, geranyl acetate, and linalyl acetate. They include, but are not limited to the phenol chavicol. They also include, but are not limited to phenol esters anethol, eugenol, and safrol, as well as other more complex compounds. Each of these compounds may be combined or reacted with procaine, lidocaine, and ephedrine, or other like anesthetic, sympathomimetic compound, or analgesic, to produce novel antimicrobial therapeutic compounds.

B. Procarvol (Procaine-carvacrol)

A preliminary synthesis of a preferred embodiment of the present invention was performed to test the feasibility and efficiency of producing the antimicrobial compounds. Standard chemistry laboratory equipment was used. The Procaine-Carvacrol compound, referred to herein as procarvol, was made using the following protocol.

The starting material procaine hydrochloride (Procaine-HCL) was converted into pure procaine by the addition of sodium hydroxide. For 40 g of procaine-HCL 325 g of 1M NaOH was added slowly in a reaction vessel with mixing on a conventional stir plate. The pH was measured throughout and reached a value up to 12.2 at 25° C. The procaine was extracted with 250 ml of chloroform by vigorous shaking. The separate phases were isolated with a separation funnel. The volatile chloroform phase was allowed to evaporate under vacuum in a standard laboratory vacuum apparatus. The resulting dry material represented the purified procaine. A yield of 32.21 g of pure procaine was obtained. The procaine was reacted with an equimolar amount of carvacrol of 26.46 g. The carvacrol was in the form of 96.44% pure essential oil of oregano and 27.43 g of this oil was used to provide the equimolar amount of carvacrol in the reaction.

Figure 4:
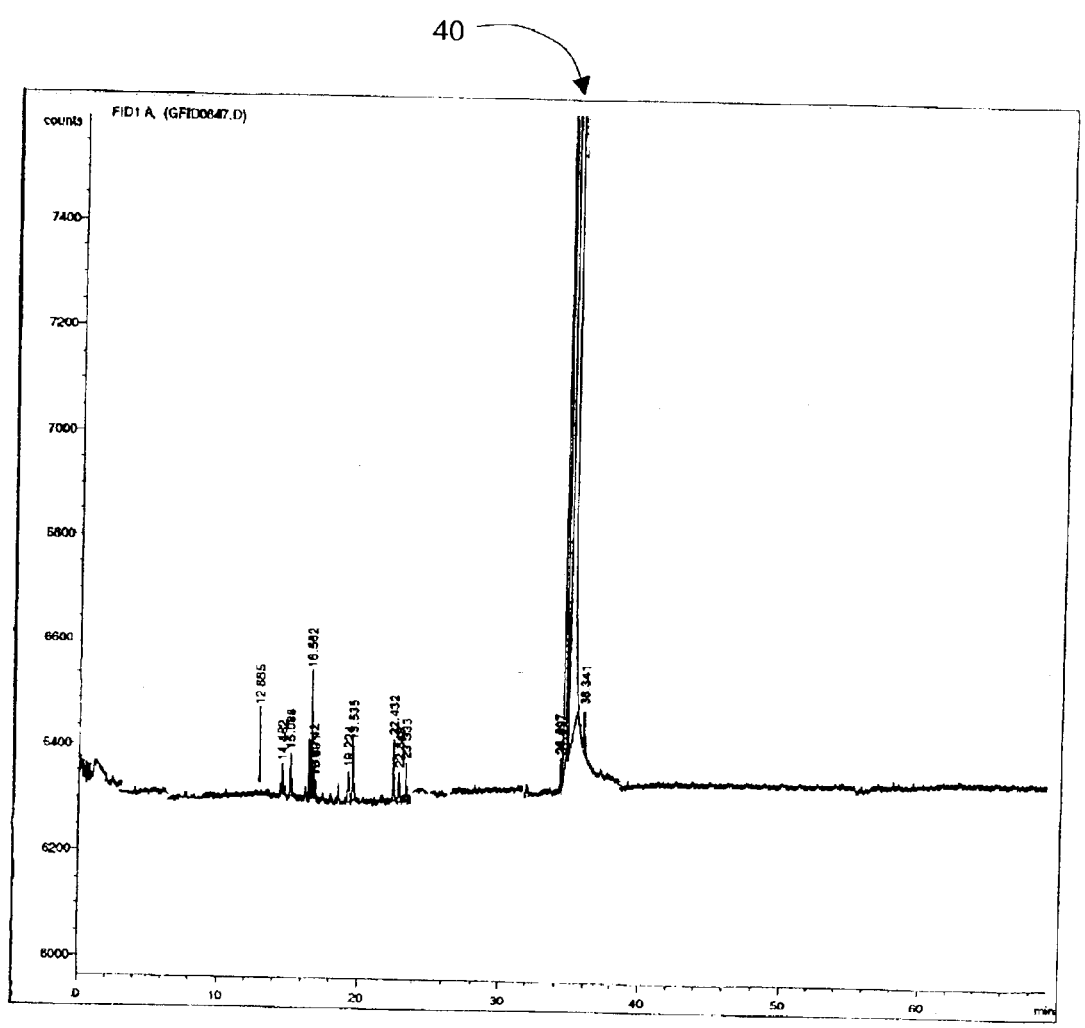
FIG. 4 illustrates the novel compound procarvol as a distinct entity via GMC chromatography. Procarvol is represented by gradient peak 40.
Figure 5:
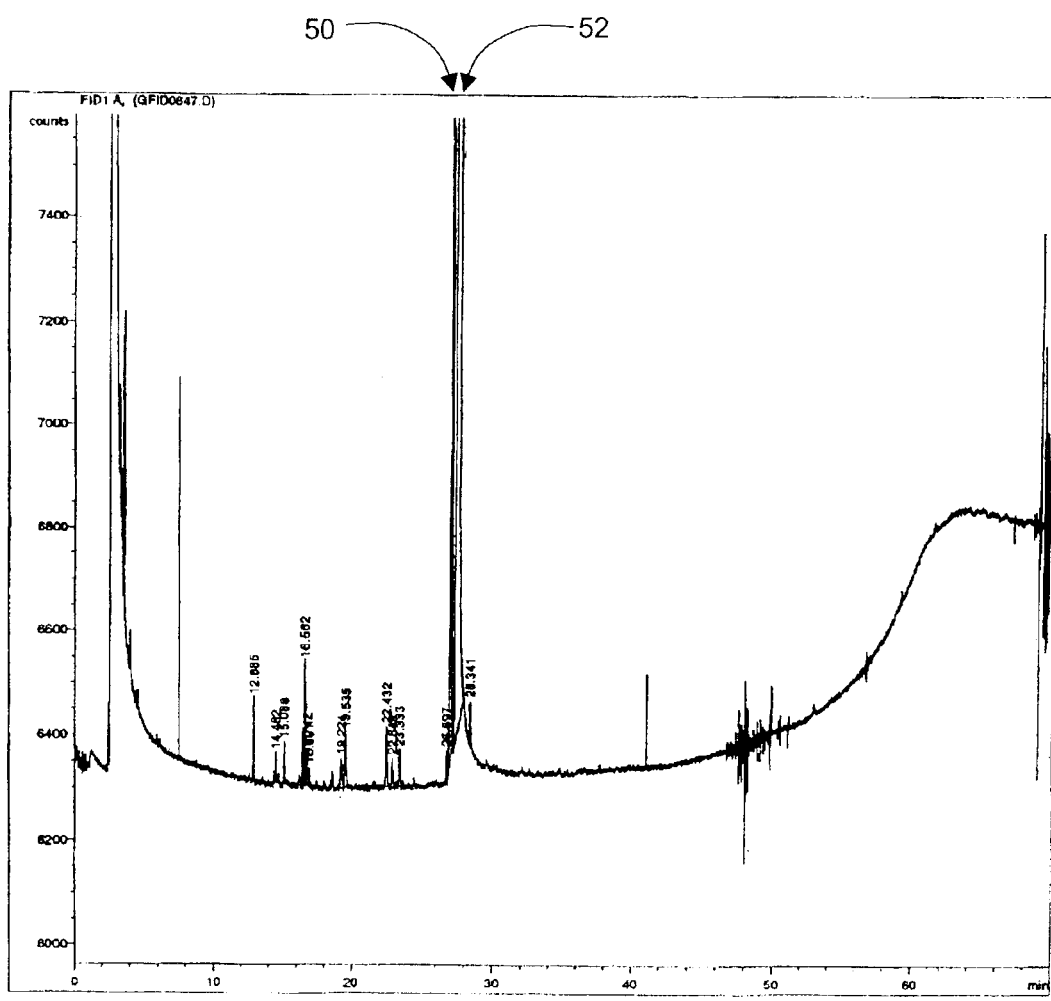
FIG. 5 shows the GMC chromatograph for the starting material oregano oil. Thymol is indicated by gradient peak 50 and carvacrol is represented by gradient peak 52.

The carvacrol was added into the procaine and the reaction vessels contents warmed in a water bath to 40° C. The contents were vigorously shaken for appropriate times, usually greater than 1 h, and the reaction allowed to slowly cool. The product compound was organoleptically equal to carvacrol. It contained a similar characteristic yellowish coloration and oder of carvacrol oil. The products of the reaction were analyzed using a gas-mass spectrophotometer. The procarvol (procaine-carvacrol) compound was made and is represented by the peak fraction 40 in FIG. 4. The procarvol peak 40 corresponds to approximately 98.82 area percentage of the entire sample. In FIG. 5 the graphical analysis of the starting material (oregano oil) is shown with thymol and carvacrol represented as peaks 50 and 52, respectively. The thymol peak 50 represented approximately 2.40 and the carvacrol peak 52 represented about 96.44 area percentages of the entire sample, respectively. The proposed chemical structure of the novel antimicrobial compound is shown in FIG. 1 (1A: Botton left, Procarvol). A similar proposed chemical structure of a second novel antimicrobial compound prothymol is also shown in FIG. 1 (1A: Bottom right).

VI. Therapeutic Pharmaceutical Compositions

The antimicrobial compound can be used alone, or as part of a therapeutic pharmaceutical composition. As used herein, the term "therapeutic pharmaceutical composition" refers to a composition which includes at least one antimicrobial compound and a pharmaceutically acceptable carrier. The term "therapeutic pharmaceutical composition" can refer to a combination of unmodified organic phenolic compounds and/or base reacted organic phenolic compound and a pharmaceutically acceptable carrier. This definition of "therapeutic pharmaceutical composition" includes essential oils obtained from plants, as well as synthetically produced organic phenolic compounds combined with acceptable carriers.

The methods of treatment of embodiments of the present invention include administering formulations through parenteral preparations to a subject. Parenteral preparations are introduced or administered directly into the body fluid systems composing the intra-or extra-cellular fluid compartments, the lymphatic system, or the blood circulatory system. Since the protective characteristics of the skin and mucous membranes are circumvented by parenteral administration, the introduction of toxic agents and microorganisms is of great concern.

Parenteral preparations can be classified into five general categories: (1) solutions ready to be injected; (2) dry products that are to be solubilized just prior to injection; (3) suspensions ready for injection; (4) dry, insoluble products ready to be combined with a carrier just prior to use, and (5) emulsions. Parenteral preparations can be administered by one or more routes, such as intravenous, subcutaneous, intradermal, intramuscular, intraspinal, intracisternal, and intrathecal. The nature and purpose of the preparation will determine the ultimate route of delivery. The specific delivery route that is chosen will place further constraints on the formulation. One advantage of parenteral administration is that it avoids inactivation by digestive processes and irregularities due to intestinal absorption.

Typically, the preparation of a parenteral formulation of a pharmaceutical begins with the selection of the carriers to be used. The carrier typically has no therapeutic activity. Absorption of the pharmaceutical from the carrier can be affected by the viscosity of the carrier, its capacity for wetting the solid particles, the solubility equilibrium produced by the carrier, and the distribution coefficient between the carrier and the aqueous system of the body. Pharmaceutically acceptable carriers are well known in the art.

Pharmaceutically acceptable carriers for parenteral preparations include distilled water; aqueous carriers such as sodium chloride injection, ringer's injection, dextrose injection, dextrose and sodium chloride injection, and lactated ringer's injection; water-miscible carriers such as ethyl alcohol, polyethylene glycol and propylene glycol; and nonaqueous carriers such as fixed oils. Ideally the fixed oil is of vegetable origin because such fixed oils tend to be metabolized, are a liquid at room temperature, and do not become rancid rapidly. The oils most commonly used are corn oil, cottonseed oil, peanut oil, and sesame oil; however, any vegetable oil that fits the above parameters may be used.

The carrier utilized in a parenteral preparation that will be injected subcutaneously, intradermally or intramuscularly is a nonaqueous carrier. More preferably, the carrier for such parenteral preparations is a highly purified olive oil, or similar compound. Other such carrier agents are well known in the art.

In the best case, the carrier utilized in a parenteral preparation that will be injected intravenously is either water or an aqueous carrier such parenteral preparations containing physiologic levels of sodium chloride. The pharmaceutical composition will be in unit dosage form. In such cases, the preparation is subdivided into unit doses containing appropriate quantities of the antimicrobial compound. The unit dosage form can be a packaged preparation, the package containing discrete quantities of preparation, for example, packaged injection amounts.

The quantity of antimicrobial compound in a unit dose may be varied or adjusted from 1 mg to 1000 mg according to the particular application. The antimicrobial compounds are typically administered at an initial dosage of about 5 mg to about 100 mg per kilogram daily. The dosages, however, may be varied depending upon the requirements of the animal being treated, the severity of the condition being treated and the compound employed. Determination of the proper dosage for a particular situation is within the skill of the art. For convenience, the total daily dosage may be divided and administered in portions during the day if desired.

VII. Illustrative Pharmaceutical Compositions Containing Antimicrobial Compound for Administration to Humans A number of different formulations of the antimicrobial compounds of the invention are possible, presented below are some illustrative examples of formulations.

A. Subcutaneous, Intradermal or Intramuscular Injection Formulation

The antimicrobial compounds can be formulated into a parenteral preparation that can be injected subcutaneously, intradermally, or intramuscularly. For such preparations, antimicrobial compound can be present at varying concentrations, for example, between 0.5 wt % to 15 wt %; 3 wt % to 10 wt %; or 5 wt % to 7.5 wt % antimicrobial compound can be combined with a carrier making up the remainder. Preferably, the carrier is nonaqueous, and more preferably it is a purified olive oil, or like material.

The antimicrobial compound and the carrier are typically combined in a mixer and mixed at 500 revolutions/minute for 5 minutes. After the formulation is mixed, it is sterilized, most ideally with ultraviolet radiation. Once the formulation has been sterilized, it is ready to be injected or packaged for storage.

B. Intravenous Injection Formulation

The antimicrobial compounds can also be formulated into a parenteral preparation that can be injected intravenously. For such preparations, the antimicrobial compound or compounds can be present at varying concentrations, for 5 example between about 0.1 wt % to about 1.0 wt %, more typically between about 0.5% to about 0.8% antimicrobial compounds with a carrier acceptable for parenteral preparations making up the remainder. Preferably, the carrier is sterilized water or an aqueous carrier, and more preferably the carrier contains 0.5 wt % to 1.0 wt % sodium chloride. The intravenous injectable-parenteral preparation is prepared by combining the antimicrobial compound or compounds with the carrier. After the formulation is mixed, it is preferably sterilized, using known methods. Once the formulation has been sterilized, it is ready to be injected or packaged for storage.

VIII. Infections

The therapeutic pharmaceutical compositions of the present invention can be used to treat a variety of internal and external infections in subjects including humans and other animals, for example, infections caused by *Escherichia* spp. including *E coli, Salmonella* spp. *Pasteurella* spp., *Staphyloccocus* spp., *Streptoccocus* spp., *Corinebacterium* spp., *Bacillus* spp., including *Bacillus anthracis, Clostridium* spp., *Spherophorus* spp., *Candida* spp., *Trychophyton* spp., *Microsporum* spp., *Micobacterium* spp., *Yibrio* spp., *Cryptosporidia* spp., *Microsporidia* spp., *Listeria monocytogenes, Lawsonia intracellularis, Treponema desynteriae, Enteroccocus* spp., *Heamophylus* spp., *Campylobacter* spp., *Chlamydia* spp., *Brucella* spp., and other pathogenic bacterial species.

The therapeutic pharmaceutical compositions of the present invention can also be used against pathogenic fungi, including, but not limited to, *Absidia* spp., *Ajellomyces* spp., *Arthroderma* spp., *Aspergillus* spp., *Blastomyces* spp., *Candida* spp., *Cladophialophora* spp., *Coccidioides* spp., *Cryptococcus* spp., *Cunninghamella* spp., *Epidermophyton* spp., *Exophiala* spp., *Filobasidiella* spp., *Fonsecaea* spp., *Fusarium* spp., *Geotrichum* spp., *Histoplasma* spp., *Hortaea* spp., *Issatschenkia* spp., *Madurella* spp., *Malassezia* spp., *Microsporum* spp., *Mucor* spp., *Nectria* spp., *Paecilomyces* spp., *Paracoccidioides* spp., *Penicillium* spp., *Pichia* spp., *Pneumocystis* spp., *Pseudallescheria* spp., *Rhizopus* spp., *Rhodotorula* spp., *Scedosporium* spp., *Schizophyllum* spp., *Sporothrix* spp., *Trichophyton* spp., and *Trichosporon* spp.

The therapeutic pharmaceutical composition of the invention can also be used against pathogenic protozoa including, but not limited to, *Cyclospora* spp., *Cryptosporidium* spp., *Microsporidium* spp., *Endamoeba histolytica, Endamoeba hartmanii, Dientamoeba fragilis, Giardia lamblia, Balantidium coli*, and *Blastocystis hominis*. They may also be used against some parasitic infections including, but not limited to helminths (nematodes).

Examples of the types of illnesses caused by microbial infections that can be treated in subjects using the pharmaceutical composition of the invention include internal infections, such as infections of the lungs (for example, pneumonia), kidneys, joints, throat, muscles, and other internal organs, such as the heart, liver, pancreas, tonsils, among others. The infections include, but are not limited to, sepsis, otitis, sinusitis, conjunctivitis, mastitis, metritis, gastro-enteritis, hepatic abscesses, urocyctitis, uretritisis caused by bacteria, yeast, fungi, or protozoa, as well as pleuritis, peritonitis, tendonitis, and wounds infected by bacteria. Other infections can also be treated, such as dermatitis and boils, also known as abscesses and furuncles, flegmonas and dermatitis. In addition secondary opportunistic infections seen typically in cases of general poor health, stress, age, or in immunologically compromised individuals, that are caused by usually non-pathogenic microorganisms, may also be treated with embodiments of the present invention. An example of this is where a primary viral infection leads to a secondary microbial infection due to taxing of the immune system. In some cases parasitic infections such as helminthiasis (nematodes) may be treated by the therapeutic compositions of the present invention.

IX. Working Examples

A. Formulation

A 10% liquid formulation of procarvol was made by reacting equimolar amounts organic carvacrol (isopropyl-o-cresol) and procaine and administered to livestock animals to establish that the formulation functioned to cure microbial infections in animals.

For Examples 1 through 14 below, the following terms or phrases, when used, have the following meanings (see FIG. 3):

Successful recovery means that the animal has improved clinical symptoms. For example, a normalization of body temperature, the animal has begun to eat if not eating before treatment, the specific symptoms (e.g., diarrhea, coughing, etc.) have ceased. In the case of mastitis, a successful recovery is found if the udder began to produce good quality milk and edemas present on the udder disappeared.

An animal was considered healthy if, for example, the body temperature was within a normal range, respiration was physiologically correct, symptoms of illness were not present, and the animal had a normal appetite. Treatments of procarvol by injection were through methods and techniques normally used by those in the agricultural field.

Figure 3:
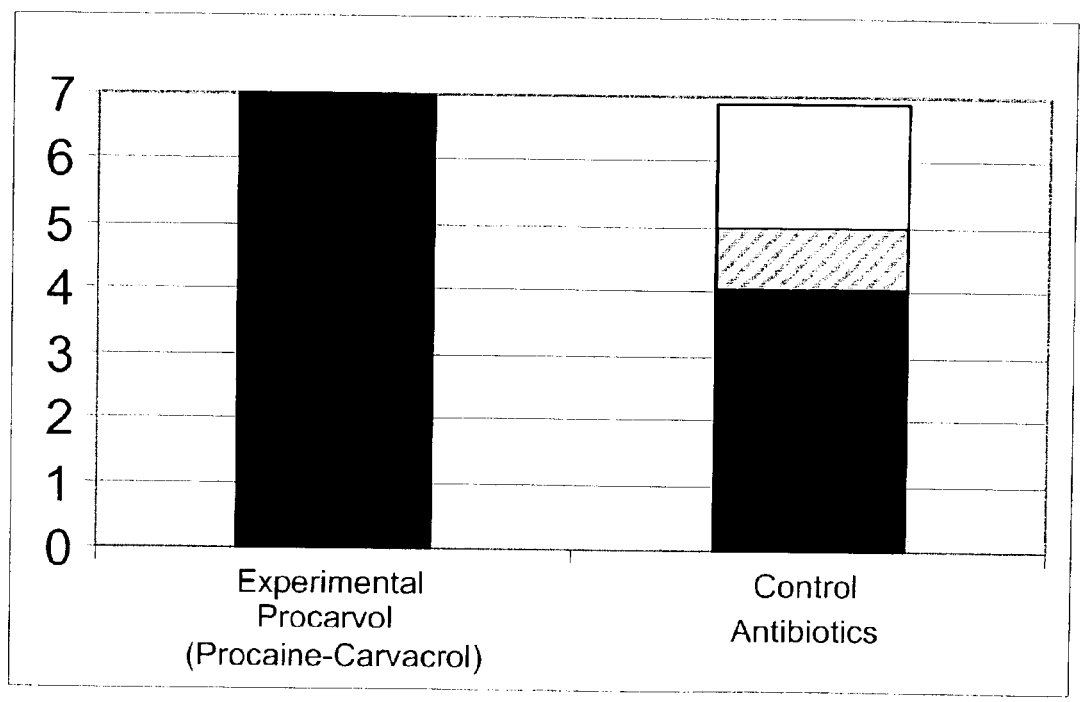
FIG. 3 is a graph that illustrates the percentage of animals that recovered from infection after treatment with a 10% liquid formulation of the present invention (experimental group, left) or with conventional antibiotics (control group, right). The black portion or the bar represents recovered animals, the right hatched indicates that longer treatment was required for recovery, and the white portion of the bar represents animals that died.

Examples are offered for a number of the animal subjects treated with a preferred formulation of the novel antimicrobial compound procarvol consisting of reacted carvacrol and procaine. Other formulations could also be used and will be assayed empirically to determine the most effective mode. In the experimental group the examples show that all of the animals recover from their infections and were healthy with an absence of clinical symptoms. These are followed by examples of a number of control animals treated by conventional veterinary methods and antibiotic agents. The control animals serve to show that conventional antibiotic treatments are not completely effective and that death can result, possibly because the pathologic bacteria are resistant to the antibiotic administered. In FIG. 3, the percentage of animals that responded to treatment is shown for the experimental group treated with a preliminary preferred formulation of the invention and the control group treated by conventional therapies. In the experimental group, all animals recovered from their infections, while the control group had several animals not respond to conventional antibiotic treatment.

B. Experimental Treatments with Procarvol

1. Experimental Group: Examples 1–7

EXAMPLE 1

In Vivo Treatment of Pneumonia in Calf

Pneumonia is a common, and frustrating problem in cattle. Pneumonia is basically an inflammation of the tissues of the lungs that results from the response of the animal to an infectious agent. The symptoms of pneumonia include an increased respiratory rate (panting), fever (a rectal temperature of over 102.5° F.), coughing, loss of appetite, and nasal discharge (mucus). The severity of pneumonia can range from mild to rapidly fatal.

The cause of pneumonia, although often attributed to a single syndrome, can have several different causes that include both viral and bacterial agents. Common viruses that can initiate pneumonia include infectious bovine rhinotracheitis virus (IBR), herpes virus, bovine respiratory syncytial virus (BRSV), parainfluenza 3 virus (PI3), certain rhinoviruses, as well as other viruses. Often, a virus will cause tissue damage, followed by invasion of the compromised tissue by bacteria. The bacterium most often involved in this pattern of infection include *Pasteurella hemolytic, Pasteurella multocida, Mycoplasma* spp., and *Antinomyces* spp.

Generally treatment of pneumonia is undertaken using antibiotics. Such treatments are generally ineffective because antibiotics have no effect on viruses, including those that cause pneumonia, and will only kill bacteria if the strain of bacteria present is susceptible to the particular antibiotic being used. Another disadvantage of antibiotics is that they must be given for a period of time, and in a dosage that is high enough to kill the bacteria so that resistance is not developed.

A one and a half (1½) month old male Angus calf with an initial weight of 317 lbs (144 kg) was afflicted with acute bronchio pneumonia. Symptoms included coughing, and fever. The calf had been positively diagnosed for pneumonia and had symptoms of fever and coughing. The calf had not been treated previously. The therapy included four (4) intramuscular injections of 10 ml of the 10% formulation of procarvol every 12 hours. The temperature of the calf over the course of treatment is shown below.

| Initial | 107° F. (42.0° C.) |
| 12 hours | 105° F. (41.0° C.) |
| 24 hours | 103° F. (39.5° C.) |
| 48 hours | 102° F. (39.0° C.) |
| Final | 102° F. (39.0° C.) |

The calf made a successful recovery and was healthy. The final weight was not measured.

EXAMPLE 2
In Vivo Treatment of Pneumonia in Pig

A three (3) month old male Landras pig with an initial weight of 92 lbs (42 kg) was afflicted with acute bronchio pneumonia. Symptoms included coughing, and fever. The pig had been positively diagnosed for pneumonia. The pig had not been treated previously. The therapy included six (6) intramuscular injections of 5 ml of the 10% formulation of procarvol every 12 hours. The temperature of the pig over the course of treatment is shown below.

| Initial | 107° F. (41.7° C.) |
| 12 hours | 104° F. (40.3° C.) |
| 24 hours | 104° F. (40.0° C.) |
| 48 hours | 102° F. (39.2° C.) |
| Final | 102° F. (38.9° C.) |

The pig made a successful recovery and was healthy. The final weight was not measured.

EXAMPLE 3
In Vivo Treatment of Mastitis in Sheep

A three (3) year old female sheep with an initial weight of 138 lbs (63 kg) was afflicted with mastitis. Symptoms included fever and edema of the udder. The sheep had been positively diagnosed for mastitis. The sheep had not been treated previously. The therapy included six (6) intramuscular injections of 7 ml of the 10% formulation of procarvol every 12 hours. The temperature of the sheep over the course of treatment is shown below.

| Initial | 107° F. (41.7° C.) |
| 12 hours | 104° F. (40.3° C.) |
| 24 hours | 104° F. (40.0° C.) |
| 48 hours | 102° F. (39.2° C.) |
| Final | 102° F. (38.9° C.) |

The sheep made a successful recovery and was healthy. The final weight was not measured.

EXAMPLE 4
In Vivo Treatment of Pneumonia in Pig

A three (3) and one half month old female Landras pig with an initial weight of 99 lbs (45 kg) was afflicted with Salmonellosis. Symptoms included fever, diarrhea, and dehydration. The pig had been positively diagnosed for the bacterium *Salmonella typhimurium*. The pig had not been treated previously. The therapy included six (6) intramuscular injections of 10 ml of the 10% formulation of procarvol every 12 hours. The temperature of the pig over the course of treatment is shown below.

| Initial | 107° F. (41.8° C.) |
| 12 hours | 105° F. (41.0° C.) |
| 24 hours | 103° F. (39.6° C.) |
| 48 hours | 102° F. (39.3° C.) |
| Final | 102° F. (39.3° C.) |

The pig made a successful recovery and was healthy. The final weight was not measured.

EXAMPLE 5
In Vivo Treatment of Kidney Inflammation in Cow

A five (5) year old female Holstein cow with an initial weight of 1078 lbs (489 kg) was afflicted with kidney inflammation. Symptoms included fever, frequent urination, and pus in the urine. The cow had been positively diagnosed for the a Streptococcus spp. bacterium. The cow had been treated previously with the antibiotic Hydrociclyne. The therapy included six (6) intramuscular injections of 40 ml of the 10% formulation of procarvol every 12 hours. The temperature of the calf over the course of treatment is shown below.

| Initial | 103° F. (39.8° C.) |
| 12 hours | 103° F. (39.6° C.) |
| 24 hours | 103° F. (39.5° C.) |
| 48 hours | 102° F. (39.2° C.) |
| Final | 102° F. (39.0° C.) |

It was noted that after the third treatment the urine was normal. The cow made a successful recovery and was healthy. The final weight was not measured.

EXAMPLE 6
In Vivo Treatment of Pneumonia in Horse

A seven (7) year old female horse with an initial weight of 1166 lbs (529 kg) was afflicted with acute bronchio pneumonia. Symptoms included coughing, fever, and difficulty breathing. The horse had been positively diagnosed for pneumonia and also had a fungal infection of *Canida albicans* in the lungs. The horse had not been treated previously. The therapy included four (4) intramuscular injections of 30 ml of the 10% formulation of procarvol every 12 hours. The temperature of the horse over the course of treatment is shown below.

| | |
|---|---|
| Initial | 103° F. (39.8° C.) |
| 12 hours | 102° F. (39.0° C.) |
| 24 hours | 101° F. (38.6° C.) |
| 48 hours | 100° F. (38.1° C.) |
| Final | 100° F. (37.8° C.) |

The horse made a successful recovery and was healthy. The final weight was not measured.

EXAMPLE 7
In Vivo Treatment of Pneumonia in Dog

One (1) seven (7) year old male dog with an initial weight of 59 lbs (27 kg) was afflicted with acute bronchio pneumonia. Symptoms included coughing, fever, and difficulty breathing. The dog had been positively diagnosed for pneumonia. The dog had not been treated previously. The therapy included four (4) intramuscular injections of 5 ml of the 10% formulation of procarvol every 12 hours. The temperature of the dog over the course of treatment is shown below.

| | |
|---|---|
| Initial | 102° F. (39.4° C.) |
| 12 hours | 101° F. (38.7° C.) |
| 24 hours | 101° F. (38.5° C.) |
| 48 hours | 100° F. (38.3° C.) |
| Final | 100° F. (38.1° C.) |

The dog made a successful recovery and was healthy. The final weight was not measured.

2. Control Group: Examples 8–14

The following examples are from a control group. These were similar animals and received standard conventional antibiotic treatment with accepted veterinary treatment protocols.

EXAMPLE 8
In Vivo Treatment of Colibacilosis in Pig

A three (3) week old female Landras pig with an initial weight of 19 lbs (9 kg) was afflicted with *Escherichia coli* colibacilosis. Symptoms included diarrhea. The pig had been positively diagnosed for the bacterium *Escherichia coli*. The pig had been treated previously with ampicillin and colicisit. The therapy included two (2) intramuscular injections of 2 ml of ampicillin every 12 hours. The temperature of the pig over the course of treatment is shown below.

| | |
|---|---|
| Initial | 108.14° F. (42.3° C.) |
| 12 hours | 108.14° F. (42.3° C.) |
| 24 hours | 107.24° F. (41.8° C.) |
| 48 hours | — — |
| Final | — — |

The pig died as a result of the infection despite conventional treatment. The final weight was not measured.

EXAMPLE 9
In Vivo Treatment of Pneumonia in Sheep

A 60 day old male sheep with an initial weight of 40 lbs (18 kg) was afflicted with acute bronchio pneumonia. Symptoms included fever and difficult breathing. The sheep had been positively diagnosed for mastitis. The sheep had been treated previously with penicillin. The therapy included 15 intramuscular injections of 2 ml Procaine penicillin G every 8 hours. The temperature of the sheep over the course of treatment is shown below.

| | |
|---|---|
| Initial | 107.24° F. (41.8° C.) |
| 12 hours | 106.7° F. (41.5° C.) |
| 24 hours | 105.3° F. (40.7° C.) |
| 48 hours | 104.2° F. (40.1° C.) |
| Final | 103.6° F. (39.8° C.) |

The sheep made a successful recovery and was healthy. The final weight was not measured.

EXAMPLE 10
In Vivo Treatment of Pneumonia in Horse

A 11 year old male horse with an initial weight of 1000 lbs (454 kg) was afflicted with acute bronchio pneumonia. Symptoms included coughing, fever, and loss of appetite. The horse had been positively diagnosed for pneumonia. The horse had been treated previously with oxytetracycline. The therapy included eight (8) intramuscular injections of 25 ml oxytetracycline every 12 hours. The temperature of the horse over the course of treatment is shown below.

| | |
|---|---|
| Initial | 102.0° F. (38.9° C.) |
| 12 hours | 101.8° F. (38.8° C.) |
| 24 hours | 101.3° F. (38.5° C.) |
| 48 hours | 100.9° F. (38.3° C.) |
| Final | 100.2° F. (37.9° C.) |

The horse made a successful recovery and was healthy. The final weight was not measured.

EXAMPLE 11
In Vivo Treatment of Pneumonia in Dog

A three (3) month old male dog with an initial weight of 25 lbs (11 kg) was afflicted with acute bronchio pneumonia. Symptoms included coughing, fever, and difficulty breathing. The dog had been positively diagnosed for pneumonia. The dog had been treated previously with sulfamethazin. The therapy included six (6) intramuscular injections of 3 ml of sulfamethazin every 12 hours. The temperature of the dog over the course of treatment is shown below.

| | |
|---|---|
| Initial | 105.4° F. (40.8° C.) |
| 12 hours | 104.7° F. (40.4° C.) |
| 24 hours | 104.0° F. (40.0° C.) |
| 48 hours | 103.8° F. (39.9° C.) |
| Final | 103.1° F. (39.5° C.) |

The dog made a successful recovery and was healthy. The final weight was not measured.

EXAMPLE 12
In Vivo Treatment of Colibacilosis in Calf

A 15 day old male Holstein calf with an initial weight of 90 lbs (41 kg) was afflicted with Escerichia coli colibacilosis. Symptoms fever, diarrhea, dehydration, and loss of appetite. The calf had been positively diagnosed for *Escherichia Coli*. The calf had not been treated previously. The therapy included five (5) intramuscular injections of 5 ml ampicillin and also the infusion of electrolytes every 12 hours. The temperature of the calf over the course of treatment is shown below.

| Initial | 107.4° F. (41.9° C.) |
|---|---|
| 12 hours | 107.4° F. (41.9° C.) |
| 24 hours | 105.4° F. (40.8° C.) |
| 48 hours | 106.3° F. (41.3° C.) |
| Final | — — |

The calf died as a result of the infection despite conventional treatment. The final weight was not measured.

EXAMPLE 13
In Vivo Treatment of Pneumonia in Pig

A three and one half (3½) month old male Landras pig with an initial weight of 80 lbs (36 kg) was afflicted with acute bronchio pneumonia. Symptoms included coughing, fever, and loss of appetite. The pig had been positively diagnosed for pneumonia. The pig had not been treated previously. The therapy included eight (8) intramuscular injections of 8 ml of ampicillin every 12 hours. The temperature of the pig over the course of treatment is shown below.

| Initial | 105.6° F. (40.9° C.) |
|---|---|
| 12 hours | 105.3° F. (40.7° C.) |
| 24 hours | 103.8° F. (39.9° C.) |
| 48 hours | 103.3° F. (39.6° C.) |
| Final | 102.4° F. (39.1° C.) |

The pig made a successful recovery and was healthy. The final weight was not measured.

EXAMPLE 14
In Vivo Treatment of Mastitis in Cow

A four (4) year old male Holstein cow with an initial weight of 1000 lbs (454 kg) was afflicted with mastitis. Symptoms included edema on the udder, and poor quality milk. The cow had been positively diagnosed for *Steptococcus uberis*. The cow had been previously treated with penicillin and streptomycin. The therapy included eight (8) intramuscular injections of 8 ml of ampicillin every 12 hours. The temperature of the cow over the course of treatment is shown below.

| Initial | 105.62° F. (40.90° C.) |
|---|---|
| 12 hours | 104.90° F. (40.50° C.) |
| 24 hours | 104.18° F. (40.10° C.) |
| 48 hours | 103.46° F. (39.70° C.) |
| Final | 102.92° F. (39.40° C.) |

The cow made a successful recovery and was healthy. The final weight was not measured.

C. Additional Treatments with Procarvol: Intramuscular Injection

The following animal study was done to determine the effectiveness of intramuscular administration of the of the 2.5% liquid formulation of procarvol. The microbial infections were in animals and consisted of a variety of internal infections, including: pneumonia, bronchitis, diarrhea of different etiologies, and arthritis. Therapy was performed on individual animals located on farms throughout the United States of America. A liquid 2.5% solution containing procarvol as the active ingredient was used.

EXAMPLE 15
Cow (Minnesota Farm).

The cow was 5 years of age and had symptoms of a painfully swollen udder, fever, with pus contaminating the milk. The bacterium *Staphylococcus aureus* was the cause of the primary infection. The diagnosis was chronic cruposa mastitis. Therapy was performed with intramuscular injections of the 2.5% formulation of procarvol. Injections of 30 ml were administered every 12 h for three days. After the course of the six treatments the infection subsided and no *Staphylococcus aureus* was detectable in the milk. The cow was active and fully recovered.

EXAMPLE 16
Sow (Iowa Farm).

The two year old sow displayed symptoms of fever, coughing, inappetence, and rhinorrhea. The diagnosis was pneumonia of unknown origin. Therapy was performed with intramuscular injections of the 2.5% formulation of procarvol. Injections of 10 ml were administered every 12 h for two days, followed by injections every 24 h for an additional two days. The sow began to recover after the second day of treatment with a significant drop in fever, reduction in coughing episodes, and improved appetite. After the course of the six treatments no signs of congestion or pneumonia were evident.

EXAMPLE 17
Horse (Wisconsin Farm).

The mare was eight years of age and displayed symptoms of fever, coughing, fatigue, rhinorrhea, and significant weight loss. The diagnosis was of pneumonia of unknown origins. Therapy was performed with intramuscular injections of the 2.5% formulation of procarvol. Injections of 20 ml were administered every 12 h for six days, for a total number of 12. The mare showed a gradual recovery. The mare became active and began to increase her movements and was observed to run after the third day of treatment. The fever dropped to normal temperature after the fourth day of treatment with a commensurate increase in appetite. Observation and auscultation over the following 15 days showed that all signs of bronchial pneumonia were gone and the mare was healthy and fully recovered.

EXAMPLE 18
Piglets (Iowa Farm).

A group of 46 piglets each approximately 18 days old showed symptoms of fever, diahrrhea, and dehydration. Microbiological testing diagnosed *Escherichia coli* hemolyticus infections in the piglet's gastrointestinal tracts. Therapy was performed with intramuscular injections of the 2.5% formulation of procarvol. Injections of 2 ml were administered per piglet each day for three days. After the therapy the entire group of piglets showed an immediate reduction in fever, improved appetite, and restoration of normal bowel function. Observations over the following week confirmed the full recovery and health of each of the 46 piglets.

EXAMPLE 19
Lambs (Idaho Farm).

A group of eight lambs each between 60–80 days of age showed symptoms of fever, diarrhea, dehydration, and loss of appetite. Microbiological testing diagnosed enterotoxemia infeciosa. The pathogenic microorganism was identified as *Clostridium perfrigens*. Therapy was performed with intramuscular injections of the 2.5% formulation of procarvol. Injections of 3 ml were administered every 12 h to each lamb for four days. After the therapy each of the lambs showed a reduction in fever, improved appetite, with elimination of all signs of diarrhea. Observation over the next seven days showed that each lamb was fully recovered and healthy.

EXAMPLE 20

Cow (Iowa Farm).

A five year old cow showed symptoms of fever together with pus in the urine of the animal. Microbiological examination identified a mixed infection of Staphyloccocus and Steptococcus species. Therapy was performed with intramuscular injections of the 2.5% formulation of procarvol. Injections of 30 ml were administered every 24 h for four 10 days. After the therapy was complete the symptoms of fever and infection were gone. Microbiological testing did not reveal any of the previously identified bacterial species over the course of 60 days, with tests on urine samples performed at day 15, 30, 45, and 60. In addition no kidney inflammation was evident during the same time period. It should be noted that the same animal was treated two times in the preceding 10 months, with conventional antibiotics for a similar infection that involved kidney inflammation, before this current treatment.

EXAMPLE 21

Horse (Pennsylvania Farm).

A gelding horse 15 years of age had difficulty walking and standing. Veterinary examination showed hoof and Achilles tendon inflammation with the accumulation of pus and edema of the joint. Identification of the causative agent was not determined. The diagnosis was of pododermatitis and tendonitis. Therapy was performed with intramuscular injections of the 2.5% formulation of procarvol. Injections of 35 ml were administered every 24 h for four seven days. Improvement in the horses walking was noticed as early as the second day of treatment. A reduction in the amount of edema was evident. The animal had a complete recovery after two weeks.

EXAMPLE 22

Dog (Veterinary Hospital Los Angeles Calif.).

An eight year old female dog had infections of the skin on the back. The diagnosis was dermatitis with infection of the hair follicles. The infection caused by a *Staphylococcus* species, which was isolated from pus derived from the dermal tissue. Therapy was performed with intramuscular injections of the 2.5% formulation of procarvol. Injections of 3 ml were administered every 24 h for four five days. After therapy the signs of infection and inflammation disappeared. Observation over 30 days confirmed a complete recovery with regeneration of hair growth in the affected areas of the animal.

EXAMPLE 23

Calves (California Farm).

A group of 37 calves each approximately 10 days old, each showed symptoms of fever, profuse diarrhea, dehydration, and appetite loss. The diagnosis was of Cryptosporidosis. Microbiological analysis revealed a protozoan intestinal infection with *Cryptosporidium parvum* as the causative microbe. Therapy was performed with intramuscular injections of the 2.5% formulation of procarvol. Injections of 5 ml were administered every 24 h for four six days. After therapy the signs of infection and inflammation disappeared. A significant amelioration of all symptoms was observed at the second day of treatment. After the complete therapy all calves in the group had a full recovery.

EXAMPLE 24

Steer (Indiana Farm).

A group of 14 steers each approximately eight months of age displayed symptoms of fever, intense coughing, loss of appetite, and weight loss. Observation revealed lung crepitation upon auscultation. Diagnosis was of viral bronchial pneumonia of the lungs in all of the animals with evidence of secondary opportunistic bacterial infections. Therapy was performed with intramuscular injections of the 2.5% formulation of procarvol. Injections of 20 ml were administered every 24 h for four five days. After therapy the fever was eliminated and the cough decreased significantly. An improved appetite was also evident. Observation of the animals over the next 45 days showed that all symptoms of the viral and secondary bacterial infections were gone.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described.

I claim:

1. A therapeutic composition for treating a microbial infection in a subject, the therapeutic composition comprising:

(a) a therapeutically effective amount of an antimicrobial compound, wherein the antimicrobial compound is procarvol formed via a chemical reaction between carvacrol and procaine, the procarvol having the following chemical structure:

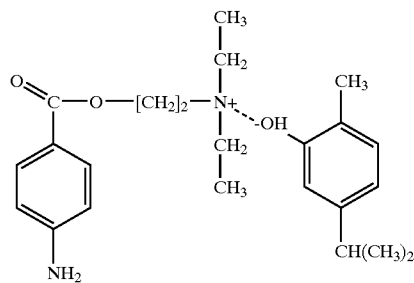

and (b) a pharmaceutically acceptable carrier.

2. A therapeutic composition for treating a microbial infection in a subject, the therapeutic composition comprising:

(a) a therapeutically effective amount of an antimicrobial compound, wherein the antimicrobial compound is prothymol formed via a chemical reaction between procaine and thymol, the prothymol having the following chemical structure:

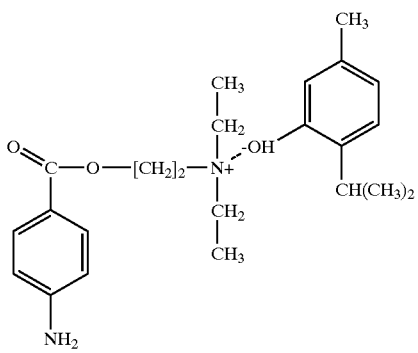

and (b) a pharmaceutically acceptable carrier.

3. A therapeutic composition for treating a microbial infection in a subject, the therapeutic composition comprising:

(a) a therapeutically effective amount of an antimicrobial compound, wherein the antimicrobial compound is formed via a chemical reaction between lidocaine and carvacrol, the antimicrobial compound having the following chemical structure:

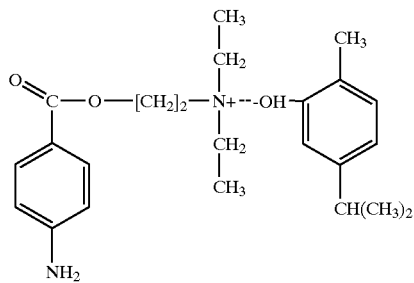

and (b) a pharmaceutically acceptable carrier.

4. A therapeutic composition for treating a microbial infection in a subject, the therapeutic composition comprising:

(a) a therapeutically effective amount of an antimicrobial compound, wherein the antimicrobial compound is formed via a chemical reaction between lidocaine and thymol, the antimicrobial compound having the following chemical structure:

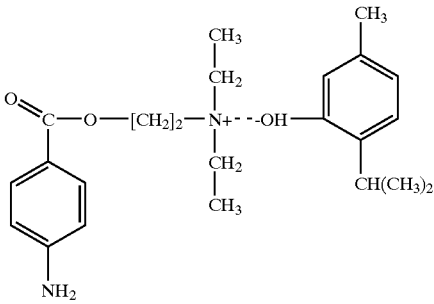

and (b) a pharmaceutically acceptable carrier.

5. The therapeutic compositions as in any of claims 1–4 further comprising an additive selected from the group consisting of vitamins, minerals, amino acids, fats, oils, and combinations thereof.

6. The therapeutic compositions as in any of claims 1–4 wherein the antimicrobial compound comprises up to about 10% of the total weight percentage of the therapeutic composition.

7. The therapeutic compositions of claim 6, wherein the microbial infection to be treated is selected from the group consisting of a bacterial infection, a yeast infection, a fungal infection, a protozoan infection, a parasitic infection, and combinations thereof.

8. The therapeutic compositions of claim 6, wherein the subject is selected from the group consisting of humans, primates, horses, cows, pigs, sheep, goats, rabbits, dogs, cats, rodents, and birds.

* * * * *